United States Patent [19]

Catalucci

[11] 4,211,883

[45] Jul. 8, 1980

[54] PROCESS FOR THE PRODUCTION OF P-(N-METHYL)-AMINOBENZOYL-L-GLUTAMIC ACID

[75] Inventor: Enrico Catalucci, Arona, Italy

[73] Assignee: Lonza, Ltd., Gampel, Switzerland

[21] Appl. No.: 926,007

[22] Filed: Jul. 19, 1978

[30] Foreign Application Priority Data

Aug. 12, 1977 [CH] Switzerland .......................... 9877/77

[51] Int. Cl.$^2$ ........................................... C07C 101/44
[52] U.S. Cl. ................................ 562/433; 260/544 N; 562/458
[58] Field of Search ................................ 562/433, 450

[56] References Cited

U.S. PATENT DOCUMENTS

| | | | |
|---|---|---|---|
| 3,551,419 | 12/1970 | Da Ra et al. ........................ | 562/450 |
| 3,892,801 | 7/1975 | Kazan ................................. | 562/450 |

OTHER PUBLICATIONS

Cosulich et al., J.A.C.S., vol. 70, pp. 1922–1926 (1948).
Fu et al., J. Org. Chem., vol. 30, pp. 1277–1278 (1965).
Santi, J. Heterocyc. Chem., vol. 4, pp. 475–481 (1967).
Seeger, J.A.C.S., vol. 71, pp. 1953–1958 (1949).
Fresin et al., Reagents for Organic Synthesis, p. 1158 (1965).
McOhme, Protective Groups in Organic Chemistry, pp. 46–53 (1974).
Abo–Sier et al., Chem. Abst., vol. 87, p. 432, #52897p (1977).

*Primary Examiner*—Norman Morgenstern
*Assistant Examiner*—James H. Reamer
*Attorney, Agent, or Firm*—Fisher, Christen & Sabol

[57] ABSTRACT

Process for the production of p-(N-methyl)-aminobenzoyl-L-glutamic acid. The process includes introducing a formyl group into p-(N-methyl)-amino-benzoic acid, with p-(N-methyl-N-formyl)-aminobenzoic acid being formed. The p-(N-methyl-N-formyl)-aminobenzoic acid is chlorinated with a chloridizing agent, such as, sulfonyl chloride or thionyl chloride, with p-(N-methyl-N-formyl)-aminobenzoic acid chloride forming. The p-(N-methyl-N-formyl)-aminobenzoic acid chloride is reacted with L-glutamic acid in the presence of a base as an acid acceptor, with p-(N-methyl-N-formyl)-amino benzoyl-L-glutamic acid forming. The p-(N-methyl-N-formyl)-amino benzoyl-L-glutamic acid is converted into p-(N-methyl)-amino benzoyl-L-glutamic acid by alkaline hydrolysis in a 2.5 to 3.5 normal caustic soda solution at 30° to 70° C. Intermediates which are obtained include: p-(N-methyl-N-formyl)-aminobenzoic acid; p-(N-methyl-N-formyl)-aminobenzoic acid chloride; and p-(N-methyl-N-formyl)-amino benzoyl-L-glutamic acid.

4 Claims, No Drawings

PROCESS FOR THE PRODUCTION OF P-(N-METHYL)-AMINOBENZOYL-L-GLUTAMIC ACID

BACKGROUND OF THIS INVENTION

1. Field of This Invention

This invention relates to a process for the production of p-(N-methyl)-amino benzoyl glutamic acid from p-(N-methyl)-amino-benzoic acid. This invention also relates to various intermediates in such process.

2. Prior Art p-(N-methyl)-amino-benzoyl glutamic acid has been made from p-iodobenzoylglutamic acid and methyl amine in the presence of caustic soda solution at a pH of 8 to 9 and a copper catalyst [Cosulich and Smith, J. Am. Chem. Soc. 70, 1922 (1948)]. The process is characterized by the very expensive iodine derivatives used as starting products, and the reproduceability of the values is not guaranteed.

According to Fu, Reiner and Loo, J. Org. Chem. 30, 1277 (1965), p-(N-methyl)-aminobenzoyl glutamic acid can be produced from p-(N-methyl)-aminobenzoic acid, which is converted into its acid chloride. The acid chloride is reacted with diethyl-L-glutamate to obtain the corresponding amino benzoyl glutamic acid ester. The latter is hydrolyzed into the acid. The (N-methyl)-amino group of the p-(N-methyl)-aminobenzoic acid is protected by reaction with carbobenzyl oxychloride. Such means that a protective agent must be used which is too expensive for an industrial scale operation. [In addition, applicants have found that the process was not reproduceable with regard to its first step. Only benzyl oxycarbonyl-methyl aminobenzoic acid which was heavily contaminated with p-(N-methyl)-aminobenzoic acid, was obtained.]

D. V. Santi, J. Heterocycl. Chem. 4, 475 (1967), teaches producing the p-(N-methyl-N-tosyl)-aminobenzoic acid, starting from ethyl-p-aminobenzoate by first achieving therefrom ethyl-p-(N-tosyl)-aminobenzoate. The latter is chlorinated into p-(N-methyl-N-tosyl)-amino benzoyl chloride. Diethyl-p-(N-methyl-N-tosyl)-amino benzoyl glutamic acid ester by reacting the latter with diethyl-L-glutamic hydrochloride. After another reaction step, the diethyl-p-(N-methyl)-aminobenzoyl-L)-glutamate is arrived at. The method is very cumbersome with regard to the large number of synthesis steps and is therefore not particularly suitable for industrial use.

BROAD DESCRIPTION OF THIS INVENTION

An object of this invention is to provide a process for the production of p-(N-methyl)-amino benzoyl-L-glutamic acid which has a relatively low cost of materials, is relatively simple in execution and is readily transferable into an industrial scale. A further object is to provide certain new intermediates. Other objects and advantages of this invention are set out herein or are obvious herefrom to one ordinarily skilled in the art.

The objects and advantages of this invention are achieved by the processes and advantages of this invention.

This invention involves a process for the production of p-(N-methyl)-amino benzoyl-L-glutamic acid which includes:

(I) introducing a formyl group into the p-(N-methyl)-amino benzoic acid;

(II) chlorinating the resultant p-(N-methyl-N-formyl)-amino benzoic acid with a chlorinating agent;

(III) converting the resultant p-(N-methyl-N-formyl)-amino benzoic acid chloride with L-glutamic acid in the presence of a base as an acid acceptor; and (IV) transforming the resultant p-(N-methyl-N-formyl)-amino benzoyl glutamic acid by alkaline hydrolysis using 2.5 to 3.5 normal caustic soda solution at 30° to 70° C. into p-(N-methyl)-amino benzoyl-L-glutamic acid.

This invention also includes the intermediates p-(N-methyl-N-formyl)aminobenzoic acid, p-(N-methyl-N-formyl)-aminobenzoic acid chloride and p-(N-methyl-N-formyl)-amino benzoyl-L-glutamic acid.

The formyl group is eminently suitable for the protection of the methyl amino function. Not only is the introduction of the formyl group accomplished with ease, but its separation (removal) is easy and is achieved without racemization of the glutamic acid moiety.

The process of this invention is based on the following reaction scheme:

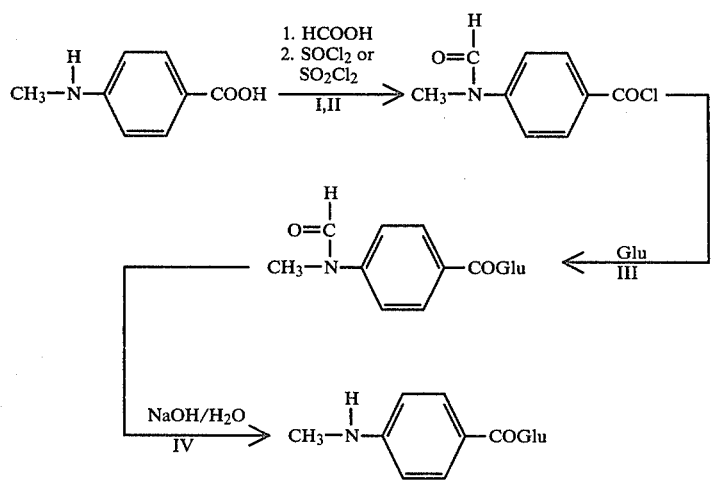

The introduction of the formyl group in the first process step (I) can be accomplished by any suitable method, but is preferably accomplished by boiling p-(N-methyl)-aminobenzoic acid in HCOOH, as a reaction medium, under reflux. The p-(N-methyl-N-formyl)- amino benzoic acid is obtained in a quantitative yield and can be isolated in a very pure form by washing with water. The p-(N-methyl-N-formyl)-aminobenzoic acid can be chlorinated in the second process step (II) by any suitable method, but is preferably alcohol with sulfonyl chloride or thionyl chloride at 40° to 80° C. Advantageously, operation with the sulfonyl chloride or thionyl chloride as reaction medium is done at a dilution of 10:1 (thionyl chloride or sulfonyl chloride to the acid) at a temperature of 60° C. However, neither such temperature nor such dilution is critical. The course of the reaction may be followed on the basis of the waste gas developed. Also, the p-(N-methyl)-aminobenzoic acid can be converted with formic acid and, after removal by distillation of any excess formic acid, the reaction product p-(N-methyl-N-formyl)-aminobenzoic acid can be treated in the same reactor with sulfonyl chloride or thionyl chloride.

The developed p-(N-methyl-N-formyl)-aminobenzoic acid chloride can then be separated by evaporation of any excess sulfonyl chloride or thionyl chloride as a crystalline substance, which is easily dissolved in an organic solvent, such as, benzene toluene methylene chloride, etc. Any suitable separation method can be used.

The acid chloride, dissolved in one of the just-mentioned organic solvents, can be dosed into an aqueous suspension of L-glutamic acid in an additional process step (III). At the same time a base, preferably not too strong of a base, is used as an acid acceptor. As such a base, a carbonate, bicarbonate, or hydroxide of Na, K, Mg, Ca or Ba, a tertiary amine, calcium oxide or magnesium oxide can be used.

The resultant p-(N-methyl-N-formyl)-amine benzoyl-L-glutamic acid for the greater part can be precipitated out after acidulation to about pH 1 as oil. The oil can be isolated by decanting. For production (recovery) of the remaining products, any one of several known methods, such as, example, liquid-liquid extraction of the aqueous mother lye, can be used.

In the last process step (IV), the formyl group is removed (separated) by alkaline or alkali hydrolysis. The alkaline hydrolysis must not take place under harsh acid conditions because of the danger of racemization of the glutamic acid moiety. As an optimum compromise between the concentration of the base and the temperature, hydrolysis of the formyl group is preferably carried out in 2.5 to 3.5 N NaOH at 30° to 70° C. The result is quantitative and without racemization. Most preferably the alkaline hydrolysis is conducted at 40° to 50° C. with 3 N NaOH. The p-(N-methyl)-amino benzoyl-L-glutamic acid can be isolated by neutralization and evaporation of the solution with subsequent methanol extraction of the residue, but there is contamination by NaCl and sodium formate. By treatment of the methanol solution with $BaCl_2$, p-(N-methyl)-amino benzoyl-L-glutamic acid can be isolated from the alkaline hydrolysis as its barium salt. On the other hand the solution from the hydrolysis which essentially contains the sodium salt of p-(N-methyl)-amino benzoyl-L-glutamic acid, sodium formate and NaOH, can also be used as such directly in the methotrexate synthesis. The p-(N-methyl)-amino benzoyl-L-glutamic acid is a fragment of the important cancer remedy methotrexate and is used as educt in the methotrexate-production process [R. R. Seeger, J. Am. Chem. Soc. 71, 1753 (1949)].

To repeat, this invention involves a process for the production of p-(N-methyl)-amino-benzoyl-L-glutamic acid. The process includes introducing a formyl group into p-(N-methyl)-aminobenzoic acid, with p-(N-methyl-N-formyl)aminobenzoic forming. The p-(N-methyl-N-formyl)-aminobenzoic acid is chlorinated with a chloridizing agent, such as, sulfonyl chloride or thionyl chloride, with p-(N-methyl-N-formyl)-aminobenzoic acid chloride forming. The p-(N-methyl-N-formyl)-aminobenzoic acid chloride is reacted with L-glutamic acid in the presence of a base as an acid acceptor, with p-(N-methyl-N-formyl)-amino benzoyl-L-glutamic acid forming. The p-(N-methyl-N-formyl)-amino benzoyl-L-glutamic acid is converted into p-(N-methyl)-amino benzoyl-L-glutamic acid by alkaline hydrolysis in a 2.5 to 3.5 normal caustic soda solution at 30° to 70° C.

This invention also includes the intermediates: p-(N-methyl-N-formyl)-aminobenzoic acid; p-(N-methyl-N-formyl)-aminobenzoic acid chloride; and p-(N-methyl-N-formyl)-amino benzoyl-L-glutamic acid.

The organic solvents useful in the separation of the developed p-(N-methyl-N-formyl)-aminobenzoic acid chloride include ketones, ethers, esters, ether-alcohols, alcohols, hydrocarbons and halogenated compounds. Specific examples of solvents include ethanol, acetone, methyl Cellosolve, methyl acetone, diethyl ketone, methyl ethyl ketone, methyl n-propyl ketone, cyclohexanone, methyl isobutyl ketone, methyl n-butyl ketone, ethyl n-butyl ketone, methyl, n-amyl ketone, diacetone alcohol, acetophenone, methyl n-hexyl ketone, diisobutyl ketone, tetrahydrofuran, 1,4-dioxane, isopropyl ether, ethyl n-butyl ether, diethyl Cellosolve, n-butyl ether, amyl ether, dibutyl Cellosolve, ethyl formate, methyl acetate, ethyl acetate, n-propyl acetate, isopropyl acetate, n-butyl acetate, sec-butyl acetate, isobutyl acetate, amyl acetate, Cellosolve acetate, Carbitol acetate, 2-ethylhexyl acetate, diethyl oxalate, Cellosolve, Dowanol 33B, Dowanol 34B, butyl Cellosolve, methyl Carbitol, Dowanol 37B, Carbitol, Dowanol 1, butyl Carbitol, Dowanol 50B, methanol, 1-propanol, 2-propanol, ethylene glycol, 1-butanol, 2-butanol, 2-methyl-1-propanol, 1,2-propanediol, amyl alcohol, 3-pentanol, isoamyl alcohol, 1,3-butanediol, furfuryl alcohol, cyclohexanol, n-hexyl alcohol, benzyl alcohol, 2-ethyl-1-butanol, 3-heptanol, 1-octanol, 2-ethyl-1-hexanol, benzene, cyclohexane, n-benzene, toluene n-heptane, xylene, ethylbenzene, n-octane, isopropylbenzene, turpentine, p-cymene, pine oil, n-butyl chloride, ethylene chloride, ethylidene chloride, amyl chloride, monochlorobenzene, propylene chloride, trichloromethane, chlorotoluene, trichloroethane, dichloropentane, o-dichlorobenzene, 1-chloro-2-ethylhexane, carbon tetrachloride, 1,1,2,2-tetrachloroethane, 1,2,4-trichlorobenzene, nitromethane, nitroethane, 1-nitropropane, 2-nitropropane, nitrobenzene, p-nitrotoluene, acetonitrile, formamide, dimethylformamide, monoethanolamine, aniline, pyridine, dimethylanaline, linseed oil and phenol. Mixtures of two or more miscrible solvents can be used.

Applicant's copending application, which was filed on the same day and which is entitled "Process For the Production of Methotrexate", is incorporated by reference, particularly the portions involving the production of methotrexate from p-(N-methyl)-amino benzoyl-L-glutamic acid.

DETAILED DESCRIPTION OF THIS INVENTION

As used herein all part, ratios and percentages are on a weight basis unless otherwise stated herein or otherwise obvious herefrom to one ordinarily skilled in the art.

EXAMPLE 1

10.0 g. (0.066 mole) of p-(N-methyl)-aminobenzoic acid was boiled under reflux free of water in 100 ml of formic acid for 3 hrs., and then evaporated to dryness. The reaction product, p-(N-methyl-N-formyl)-aminobenzoic acid, can be isolated in pure form (white crystals having a melting point of 218° C.) by suspension in water or preferably by reprecipitation in water or preferably by reprecipitation by means of NaOH/HCl at 97 percent yield. Or the reaction product can be directly used as raw material in the next step.

The raw product of the formylization step was suspended in 140 ml of thionyl chloride and heated to 60° C. until everything went into solution and no waste gases were developed under vacuum by distillation. The residue was subsequently dissolved in 60 ml of benzene, and used in the next process step as a yellow solution. Proof of the quantitative nature of this reaction was the absence of crystals of p-(N-methyl-N-formyl)-aminobenzoic acid which were insoluble in benzene.

A suspension of 10.6 g of MgO and 14.2 of L-glutamic acid (0.096 mole) in 100 ml $H_2O$ was stirred for 1 hour at 70° C., then cooled to 30° C. The suspension was mixed drop by drop while stirring in the course of about 15 min. with the benzene solution of p-(N-methyl-N-formyl)-aminobenzoic acid chloride from the prior process step. The mixture was stirred overnight at room temperature. After separation of the layers, the aqueous phase was adjusted by means of concentrated HCl to pH 1 and allowed to stand overnight. The layer of oil formed thereby, which consisted essentially of p-(N-methyl-N-formyl)-amino benzoyl-L-glutamic acid was separated from the aqueous mother lye. The p-(N-methyl-N-formyl)-amino benzoyl-L-glutamic acid obtained amounted to 11.5 g (56 percent of theory, related to the amount of p-(N-methyl)-aminobenzoic acid used).

According to HPLC (High Pressure Liquid Chromatograply) there were only traces of p-(N-methyl)-aminobenzoic acid and p-(N-methyl-N-formyl)-aminobenzoic acid (<1 percent yield) in the mother lye. The chief components were p-(N-methyl-N-formyl)-amino benzoyl-L-glutamic acid and the p-(N-methyl)-amino benzoyl-L-glutamic acid formed by acid hydrolysis in the ratio of 3:1. So in this reaction step, therefore, the yield of p-(N-methyl-N-formyl)-amino benzoyl-L-glutamic acid amounted to 89 percent and of p-(N-methyl)-amino benzoyl-L-glutamic acid to about 11 percent, related to the amount of p-(N-methyl)-aminobenzoic acid used.

The isolated oil from the prior process step was now stirred well in 90 ml of 3 N NaOH and the developed suspension was stirred at 40° to 52° C. for 1 hour. HPLC analysis showed that p-(N-methyl)-amino benzoyl-L-glutamic acid had formed quantitatively after this time as the Na-salt and also that no separation of the glutamic acid part had taken place. This solution could be used directly in the methotrexate synthesis.

In order to determine the optical purity of the p-(N-methyl)-amino benzoyl-L-glutamic acid, it was isolated as follows: The hydrolysis solution was adjusted to pH 6 by means of concentrated HCl and evaporated to dryness under vacuum. The residue was suspended in 300 ml of methanol and stirred for 3 hours, and then filtered off. The clear filtrate was concentrated under vacuum until it became milky, and was mixed with a 0.5 M $BaCl_2$ solution in $H_2O$/MeOH(1:1) until no further product was precipitated out. After filtration and drying, 15 g (48 percent) of the Ba-salt of p-(N-methyl)-amino benzoyl-L-glutamic acid was obtained which still contained traces of Ba-formate and $BaCl_2$. 10 g of it was reprecipitated from $H_2O$/MeO and 7 g of pure (>98 percent) Ba-salt p-(N-methyl)-amino benzoyl-L-glutamic acid dihydrate was obtained.

12 g of the crude Ba-salt of p-(N-methyl)-amino benzoyl-L-glutamic acid was stirred in 120 ml of 20 percent HCl in absolute ethanol for 3 days, was later mixed with 200 ml of $H_2O$ and then mixed with concentrated $NH_4OH$ to pH 7.5. After extraction with ether and drying, and subsequent evaporation of the ether, a residue was obtained. The residue, after recrystallization from alcohol/$H_2O$, produced 6.3 g of the diethyl ester of p-(N-methyl)-amino benzoyl-L-glutamic acid in the form of white crystals. The product had a melting point of 90° C. and the $(\alpha)_D^{20}$ (in 1 N HCl) was $-19.8°$ C. [The literature melting point is 89.8° to 91° C. and the $(\alpha)_D^{20}$ (in 1 N HCl) is $-20.5°$ C.].

EXAMPLE 2

Example 1 was repeated using sulfonyl chloride in place of thionyl chloride.

What is claimed is:

1. The process for the production of p-(N-methyl)-aminobenzoyl-L-glutamic acid which comprises:
   (a) introducing a formyl group into p-(N-methyl) aminobenzoic acid by boiling the p-(N-methyl)-aminobenzoic acid in HCOOH, as a reaction medium, under reflux, whereby p-(N-methyl-N-formyl)-aminobenzoic acid in formed;
   (b) chlorinating the p-(N-methyl-N-formyl)-aminobenzoic acid with a chlorinating agent, which is sulfonyl chloride or thionyl chloride, at 40° to 80° C., whereby p-(N-methyl-N-formyl)-aminobenzoic acid chloride is formed;
   (c) reacting the p-(N-methyl-N-formyl)-aminobenzoic acid with L-glutamic acid in the presence of a base as an acid acceptor, whereby p-(N-methyl-N-formyl)-amino benzoyl-L-glutamic acid is formed; and
   (d) converting the p-(N-methyl-N-formyl)-amino benzoyl-L-glutamic acid into p-(N-methyl)-amino benzoyl-L-glutamic acid by alkaline hydrolysis in a 2.5 to 3.5 normal caustic soda solution at 30° to 70° C.

2. The process as claimed in claim 1 wherein, in step (a) the formyl group is introduced by boiling the p-(N-methyl)-aminobenzoic acid in HCOOH, as a reaction medium, under reflux.

3. The process as claimed in claim 1 wherein, in step (b), the p-(N-methyl-N-formyl)-aminobenzoic acid is chlorinated with sulfonyl chloride or thionyl chloride at 40° to 80° C.

4. The process as claimed in claim 1 wherein, in step (c), the p-(N-methyl-N-formyl)-aminobenzoic acid chloride is mixed with L-glutamic acid in the presence of a carbonate of Na, K, Mg, Ca or Ba, a bicarbonate of Na, K, Mg, Ca or Ba, a hydroxide of Na, K, Mg, Ca or Ba, a tertiary amine, calcium oxide, magnesium oxide, or a mixture of two or more of such components.

* * * * *